United States Patent [19]

Tada

[11] 3,971,784

[45] July 27, 1976

[54] 5-FLUOROURACIL DERIVATIVES

[75] Inventor: Masao Tada, Sendai, Japan

[73] Assignee: Mitsui Pharmaceuticals, Incorporated, Tokyo, Japan

[22] Filed: Nov. 25, 1974

[21] Appl. No.: 527,143

[30] Foreign Application Priority Data
Nov. 28, 1973 Japan.............................. 48-132795
Nov. 28, 1973 Japan.............................. 48-132796

[52] U.S. Cl. ...................... 260/256.5 R; 260/260; 424/251
[51] Int. Cl.² ........................................ C07D 239/54
[58] Field of Search ..................... 260/260, 256.5 R

[56] References Cited
UNITED STATES PATENTS
3,360,520   12/1967   Luckenbaugh et al. ............ 260/260

Primary Examiner—Paul M. Coughlan, Jr.
Attorney, Agent, or Firm—Fisher, Christen & Sabol

[57] ABSTRACT

5-Fluorouracil derivatives represented by the formula

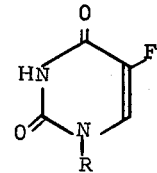

wherein R is arylcarbonyl, substituted arylcarbonyl, heterocyclic carbonyl, alkylsulfonyl, arylsulfonyl, substituted arylsulfonyl, heterocyclic sulfonyl or alicyclic sulfonyl are effective antimetabolites useful in mammary gland or gastrointestinal cancer therapy.

27 Claims, No Drawings

5-FLUOROURACIL DERIVATIVES

BACKGROUND OF THE INVENTION

1. Field of the Invention

The present invention relates to 5-fluorouracil derivatives and, more particularly, to novel 5-fluorouracil derivatives represented by the formula

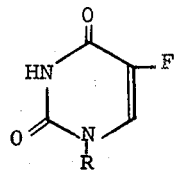

wherein R represents arylcarbonyl, substituted arylcarbonyl, heterocyclic carbonyl, alkylsulfonyl, arylsulfonyl, substituted arylsulfonyl, heterocyclic sulfonyl or alicyclic sulfonyl.

DESCRIPTION OF THE PRIOR ART

5-Fluorouracil is well known to be an effective anti-metabolite used as an agent for mammary gland or gastrointestinal cancer therapy. However, because of its high toxicity, 5-fluorouracil is not considered to be a favorable anti-cancer agent and improvement has been recognized as necessary. On the other hand, as a low toxic 5-fluorouracil derivative, there is known 5-fluoro-1-(2-tetrahydrofuryl)uracil which has been used as an anti-tumor agent. However, this compound is substantially inferior to 5-fluorouracil in anti-tumor activity and it has been desired to develop 5-fluorouracil derivatives which are as non-toxic as 5-fluoro-1-(2-tetrahydrofuryl)uracil and are also substantially more effective anti-metabolites.

SUMMARY OF THE INVENTION

The 5-fluorouracil derivatives of the present invention are more effective anti-metabolites than 5-fluoro-1-(2-tetrahydrofuryl)uracil and are as low in toxicity as that prior art compound. The 5-fluorouracil derivatives of the present invention may be prepared in various ways.

DESCRIPTION OF THE PREFERRED EMBODIMENT

The 5-fluorouracil derivatives of the formula

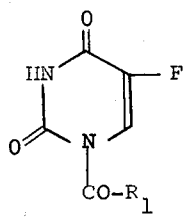

wherein $R_1$ represents aryl containing from 6 to 10 carbon atoms, halogen substituted aryl, alkyl and alkoxy substituted aryl wherein the alkyl or alkoxy group contains from 1 to 6 carbon atoms, nitro substituted aryl or a heterocyclic group are prepared by acylating 5-fluorouracil with acyl halides of the formula $$R_1\text{---COX}$$

wherein $R_1$ represents the same groups described above and X represents halogen.

Similarly the 5-fluorouracil derivatives of the formula

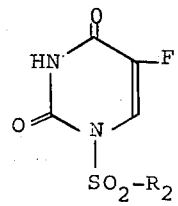

wherein $R_2$ represents alkyl containing from 1 to 6 carbon atoms, aryl containing from 6 to 10 carbon atoms, alkyl substituted aryl wherein the alkyl group contains from 1 to 6 carbon atoms, halogen substituted aryl, nitro substituted aryl, amido substituted aryl, a heterocyclic group or an alicyclic group are prepared by condensing 5-fluorouracil with sulfonyl halides of the formula $$R_2\text{---}SO_2X$$

wherein $R_2$ represents the same groups described above and X represents halogen.

The above-described acylation or condensation of 5-fluorouracil is ordinarily carried out in an organic solvent. Organic solvents such as dioxane, dimethyl sulfoxide, dimethyl formamide, dimethyl acetamide, acetonitrile, and the like are suitable for this purpose. 5-Fluorouracil is dissolved or suspended in the organic solvent, one of the above-described halides is added thereto and the reaction mixture is stirred at a temperature ranging from room temperature to the reflux temperatures of the reaction mixture. The reaction is preferably carried out in the presence of an acid acceptor of the halogen halide formed during the reaction. Such acid acceptors include, for example, triethylamine, pyridine, potassium carbonate, sodium bicarbonate, sodium hydride, and the like. The reaction mixture is preferably concentrated under reduced pressure, the residue is dissolved again in an organic solvent and, after cooling, the resultant crystals are filtered off.

The 5-fluorouracil derivatives thus obtained are white needles, leaflets or granules and are excellent as anti-cancer agents.

The following Examples illustrate methods of preparing the 5-fluorouracil derivatives of the present invention.

EXAMPLE 1

2.6 g (0.02 mole) of 5-fluorouracil was suspended in a mixed solution of 40 ml. of dioxane and 10 ml. of triethylamine. 8.4 g (0.04 mole) of p-chlorobenzoyl chloride was added to the suspension and stirred at 80°C. for 6 hours. The reaction mixture was cooled to room temperature and filtered. The filtrate was evaporated to dryness under reduced pressure and 2.7 g of residue was obtained. The residue was extracted with absolute alcohol and the extract was concentrated by evaporation. After cooling to room temperature, the resulting crystals were filtered and dried to give 1-(p-chlorobenzoyl)-5-fluorouracil weighing 1.18 g (35.1% yield). Recrystallization thereof from ethanol gave needles melting at 185°–186°C. Results of an elementary analysis were well in agreement with the calculated value as follows:

|  | C | H | Cl | F | N |
|---|---|---|---|---|---|
| Found (%) | 49.38 | 2.54 | 13.13 | 7.10 | 10.29 |
| Calcl. (%) | 49.18 | 2.25 | 13.22 | 7.08 | 10.43 |
|  | (for $C_{11}H_6ClFN_2O_3$) | | | | |

EXAMPLE 2

1.3 g (0.01 mole) of 5-fluorouracil was suspended in a mixed solution of 40 ml. of dioxane and 2 ml. of pyridine. 1.7 g (0.01 mole) of p-methoxybenzoyl chloride in 5 ml. of dioxane was added to the suspension and stirred at 80°C. for 5 hours. The reaction mixture was cooled to room temperature and filtered. The filtrate was concentrated under reduced pressure and a resinous residue was obtained. The residue was dissolved in ethanol and filtered. After cooling to 0°C., the resulting crystals were filtered and dried to give 1.30 g (49.2% yield) of 5-fluoro-1-(p-methoxybenzoyl)uracil. The product was recrystallized from dioxane-ethanol and white needles melting at 200°–201°C. were obtained. The results of an elementary analysis thereof were well in agreement with the calculated value as follows:

|  | C | H | F | N |
|---|---|---|---|---|
| Found (%) | 54.56 | 3.62 | 7.18 | 10.35 |
| Calcd. (%) | 54.55 | 3.43 | 7.20 | 10.60 |
|  | (for $C_{12}H_9FN_2O_4$) | | | |

EXAMPLE 3

2.6 g (0.02 mole) of 5-fluorouracil was reacted with 9.28 g (0.05 mole) of p-nitrobenzoyl chloride in the same manner as in Example 1 and 2.95 g (52.9% yield) of 5-fluoro-1-(p-nitrobenzoyl)uracil was obtained. The product was recrystallized from ethanol and white needles melting at 182°–183°C. were obtained. The results of an elementary analysis of the above crystals were well in agreement with the calculated value as follows:

|  | C | H | F | N |
|---|---|---|---|---|
| Found (%) | 47.50 | 2.25 | 6.79 | 15.19 |
| Calcd. (%) | 47.32 | 2.17 | 6.81 | 15.05 |
|  | (for $C_{12}H_9FN_3O_4$) | | | |

EXAMPLE 4

2.6 g (0.02 mole) of 5-fluorouracil was suspended in a mixed solution of 35 ml. of dioxane and 10 ml. of pyridine and reacted with 6.7 g (0.048 mole) of benzoylchloride. The reaction mixture was treated in the same manner as in Example 1 and 2.00 g (42.5% yield) of 1-benzoyl-5-fluorouracil was obtained. The product was recrystallized from ethanol to give white needles melting at 170°–172°C. The results of an elementary analysis thereof were well in agreement with the calculated value as follows:

|  | C | H | F | N |
|---|---|---|---|---|
| Found (%) | 56.68 | 3.01 | 8.07 | 11.83 |
| Calcd. (%) | 56.42 | 3.01 | 8.12 | 11.96 |
|  | (for $C_{11}H_7FN_2O_3$) | | | |

Other acylated 5-fluorouracil derivatives of the present invention prepared in a similar manner are summerized in Table 1 below.

TABLE 1

| Ex. No. | Compound | M.P. (°C) |
|---|---|---|
| 5 | 5-fluoro-1-(p-methylbenzoyl)uracil | 198–199 |
| 6 | 5-fluoro-1-(o-methoxybenzoyl)uracil | 183–184 |
| 7 | 1-(2,4-dichlorobenzoyl)-5-fluorouracil | 175–177 |
| 8 | 5-fluoro-1-(o-methylbenzoyl)uracil | 179–180 |
| 9 | 5-fluoro-1-(2-furoyl)uracil | 166–167 |

EXAMPLE 10

2.6 g. (0.02 mole) of 5-fluorouracil and 1.52 g (0.011 mole) of anhydrous potassium carbonate were suspended in 50 ml. of dioxane and then 2.53 g (0.022 mole) of methanesulfonyl chloride in 20 ml. of dioxane was dropwise added thereto. After stirring at 80°C. for 10 hours, the reaction mixture was filtered. The filtrate was concentrated under reduced pressure and a resinous residue was obtained. The residue was dissolved in a small amount of methanol and allowed to stand at 0°C. overnight. There was obtained 1.48 g (45.4% yield) of 5-fluoro-1-methanesulfonyluracil. Recrystallization of the product from methanol gave leaflets melting at 223°–224°C. The results of an elementary analysis thereof were well in agreement with the calculated value as follows:

|  | C | H | F | N | S |
|---|---|---|---|---|---|
| Found (%) | 28.64 | 2.42 | 9.15 | 13.28 | 15.37 |
| Calcd. (%) | 28.85 | 2.42 | 9.13 | 13.46 | 15.38 |
|  | (for $C_5H_5FN_2O_4S$) | | | | |

EXAMPLE 11

2.6 g (0.02 mole) of 5-fluorouracil and 1.38 g (0.01 mole) of anhydrous potassium carbonate were suspended in 70 ml. of dioxane. 3.5 g (0.02 mole) of benzenesulfonyl chloride in 10 ml. of dioxane was dropwise added thereto and stirred at 80°C. for 7 hours. The reaction mixture was cooled to room temperature and filtered. The filtrate was concentrated under reduced pressure and a resinous residue was obtained. The residue was dissolved in a small amount of ethanol and allowed to stand at 5°C. overnight. There was obtained 2.95 g (54.6% yield) of 1-benzenesulfonyl-5-fluorouracil. The product was recrystallized from dioxane-ethanol and gave granular crystals melting at 256°–257°C. The results of an elementary analysis thereof were well in agreement with the calculated value as follows:

|  | C | H | F | N | S |
|---|---|---|---|---|---|
| Found (%) | 44.58 | 2.53 | 7.13 | 10.06 | 11.81 |
| Calcd. (%) | 44.44 | 2.61 | 7.04 | 10.37 | 11.85 |
|  | (for $C_{10}H_7FN_2O_4S$) | | | | |

EXAMPLE 12

2.6 g (0.02 mole) of 5-fluorouracil and 1.28 g (0.01 mole) of anhydrous potassium carbonate were suspended in 50 ml. of dioxane and reacted with 3.82 g (0.02 mole) of p-toluenesulfonyl chloride in the same manner as in Example 10. There was obtained 3.54 g (62.3% yield) of 5-fluoro-1-(p-toluenesulfonyl)uracil. Recrystallization of the product from methanol-chloroform gave leaflets melting at 241°–242°C. The results of an elementary analysis thereof were well in agreement with the calculated value as follows:

| | C | H | F | N | S |
|---|---|---|---|---|---|
| Found (%) | 46.47 | 3.31 | 6.64 | 9.55 | 11.25 |
| Calcd. (%) | 46.48 | 3.19 | 6.69 | 9.86 | 11.27 |
| | (for $C_{11}H_9FN_2O_4S$) | | | | |

Other sulfonylated 5-fluorouracil derivatives of the present invention prepared in a similar manner are summerized in Table 2 below.

TABLE 2

| Ex. No. | Compound | M.P. (°C) |
|---|---|---|
| 13 | 5-fluoro-1-(o-methylbenzenesulfonyl)uracil | 204–205 |
| 14 | 1-ethylsulfonyl-5-fluorouracil | 214–215 |
| 15 | 1-(p-chlorobenzenesulfonyl)-5-fluorouracil | 237–238 |
| 16 | 5-fluoro-1-(p-iodobenzenesulfonyl)uracil | 253–254 |
| 17 | 1-(p-ethylbenzenesulfonyl)-5-fluorouracil | 215–216 |
| 18 | 1-(p-acetamidobenzenesulfonyl)-5-fluorouracil | 240–241 |
| 19 | 5-fluoro-1-(2,4,6-trimethylbenzenesulfonyl)uracil | 232–233 |
| 20 | 5-fluoro-1-(o-nitrobenzenesulfonyl)uracil | 229–231 |
| 21 | 5-fluoro-1-(naphthalene-β-sulfonyl)uracil | 218–221 |
| 22 | 1-(p-bromobenzenesulfonyl)-5-fluorouracil | 247–248 |
| 23 | 5-fluoro-1-(2-thiophenesulfonyl)uracil | 222–223 |
| 24 | 5-fluoro-1-(8-quinolinesulfonyl)uracil | 272–273 |
| 25 | 1-(d-camphorsulfonyl)-5-fluorouracil | 153–160 |

The anti-tumor activities of the 5-fluorouracil derivatives of the present invention were measured according to the procedure set forth below, and compared with that of well known 5-fluoro-1-(2-tetrahydrofuryl)uracil.

Procedure for the Measurement of Anti-tumor Activity $BDF_1$ mice weighing 18–20 g and caused to have lymphatic leukemia (L-1210) were used for this purpose. Each test compound and 5-fluoro-1-(2-tetrahydrofuryl)uracil as a standard was administered intraperitoneally to the mice at a daily dosage of 30 mg/Kg for 5 days and the percent Increased Life Span (ILS%) was observed.

The results of the above-described anti-tumor activity measurements made according to the above procedure are summarized in Table 3.

TABLE 3

| Compound | ILS(%) |
|---|---|
| 5-fluoro-1-(2-tetrahydrofuryl)uracil (Standard) | 100 |
| 1-(p-chlorobenzoyl)-5-fluorouracil | 151 |
| 5-fluoro-1-(p-methoxybenzoyl)uracil | 145 |
| 5-fluoro-1-(p-nitrobenzoyl)uracil | 136 |
| 1-benzoyl-5-fluorouracil | 163 |
| 5-fluoro-1-(p-methylbenzoyl)uracil | 137 |
| 5-fluoro-1-(o-methoxybenzoyl)uracil | 135 |
| 1-(2,4-dichlorobenzoyl)-5-fluorouracil | 133 |
| 5-fluoro-1-(o-methylbenzoyl)uracil | 134 |
| 5-fluoro-1-(2-furoyl)uracil | 125 |
| 5-fluoro-1-methanesulfonyluracil | 96 |
| 1-benzenesulfonyl-5-fluorouracil | 144 |
| 5-fluoro-1-(p-toluenesulfonyl)uracil | 141 |
| 5-fluoro-1-(o-methylbenzenesulfonyl)uracil | 102 |
| 1-ethylsulfonyl-5-fluorouracil | 132 |
| 1-(p-chlorobenzenesulfonyl)-5-fluorouracil | 138 |
| 5-fluoro-1-(p-iodobenzenesulfonyl)uracil | 108 |
| 1-(p-ethylbenzenesulfonyl)-5-fluorouracil | 129 |
| 1-(p-acetamidobenzenesulfonyl)-5-fluorouracil | 104 |
| 5-fluoro-1-(2,4,6-trimethylbenzenesulfonyl)uracil | 148 |
| 5-fluoro-1-(o-nitrobenzenesulfonyl)uracil | 138 |
| 5-fluoro-1-(naphthalene-β-sulfonyl)uracil | 146 |
| 1-(p-bromobenzenesulfonyl)-5-fluorouracil | 121 |
| 5-fluoro-1-(2-thiophenesulfonyl)uracil | 102 |
| 5-fluoro-1-(8-quinolinesulfonyl)uracil | 109 |
| 1-(d-camphorsulfonyl)-5-fluorouracil | 106 |

What is claimed is:

1. A 5-fluorouracil derivative represented by the formula

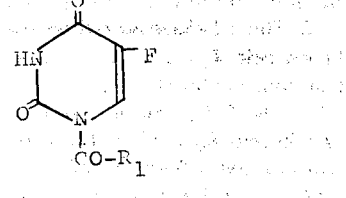

wherein $R_1$ represents phenyl, halogen substituted phenyl, nitro substituted phenyl, methylphenyl, methoxyphenyl or 2-furyl.

2. The 5-fluorouracil derivative according to claim 1 wherein $R_1$ is p-chlorophenyl and the compound is 1-(p-chlorobenzoyl)-5-fluorouracil.

3. The 5-fluorouracil derivative according to claim 1 wherein $R_1$ is p-methoxyphenyl and the compound is 5-fluoro-1-(p-methoxybenzoyl)uracil.

4. The 5-fluorouracil derivative according to claim 1 wherein $R_1$ is p-nitrophenyl and the compound is 5-fluoro-1-(p-nitrobenzoyl)uracil.

5. The 5-fluorouracil derivative according to claim 1 wherein $R_1$ is phenyl and the compound is 1-benzoyl-5-fluorouracil.

6. The 5-fluorouracil derivative according to claim 1 wherein $R_1$ is p-methylphenyl and the compound is 5-fluoro-1-(p-methylbenzoyl)uracil.

7. The 5-fluorouracil derivative according to claim 1 wherein $R_1$ is o-methoxyphenyl and the compound is 5-fluoro-1-(o-methoxybenzoyl)uracil.

8. The 5-fluorouracil derivative according to claim 1 wherein $R_1$ is 2,4-dichlorophenyl and the compound is 1-(2,4-dichlorobenzoyl)-5-fluorouracil.

9. The 5-fluorouracil derivative according to claim 1 wherein $R_1$ is o-methylphenyl and the compound is 5-fluoro-1-(o-methylbenzoyl)uracil.

10. The 5-fluorouracil derivative according to claim 1 wherein $R_1$ is 2-furyl and the compound is 5-fluoro-1-(2-furoyl)uracil.

11. A 5-fluorouracil derivative represented by the formula

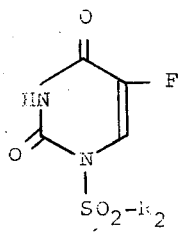

wherein R$_2$ represents methyl, ethyl, phenyl, methyl or ethyl substituted phenyl, halogen substituted phenyl, nitro substituted phenyl, acetamido substituted phenyl, naphthyl, thiofuryl, quinolyl or camphoryl.

12. The 5-1-fluorouracil derivative according to claim 11 wherein R$_2$ is methyl and the compound is 5-fluoro-1-methanesulfonyluracil.

13. The 5-fluorouracil derivative according to claim 11 wherein R$_2$ is phenyl and the compound is 1-benzenesulfonyl-5-fluorouracil.

14. The 5-fluorouracil derivative according to claim 11 wherein R$_2$ is p-tolyl and the compound is 5-fluoro-1-(p-toluenesulfonyl)uracil.

15. The 5-fluorouracil derivative according to claim 11 wherein R$_2$ is o-methylphenyl and the compound is 5-fluoro-1-(o-methylbenzenesulfonyl)uracil.

16. The 5-fluorouracil derivative according to claim 11 wherein R$_1$ is ethyl and the compound is 1-ethylsulfonyl-5-fluorouracil.

17. The 5-fluorouracil derivative according to claim 11 wherein R$_2$ is p-chlorophenyl and the compound is 1-(p-chlorobenzenesulfonyl)-5-fluorouracil.

18. The 5-fluorouracil derivative according to claim 11 wherein R$_2$ is p-iodophenyl and the compound is 5-fluoro-1-(p-iodobenzenesulfonyl)uracil.

19. The 5-fluorouracil derivative according to claim 11 wherein R$_2$ is p-ethylphenyl and the compound is 1-(p-ethylbenzenesulfonyl)-5-fluorouracil.

20. The 5-fluorouracil derivative according to claim 11 wherein R$_2$ is p-acetamidophenyl and the compound is 1-(p-acetamidobenzenesulfonyl)-5-fluorouracil.

21. The 5-fluorouracil derivative according to claim 11 wherein R$_2$ is 2,4,6-trimethylphenyl and the compound is 5-fluoro-1-(2,4,6-trimethylbenzenesulfonyl)uracil.

22. The 5-fluorouracil derivative according to claim 11 wherein R$_2$ is o-nitrophenyl and the compound is 5-fluoro-1-(o-nitrobenzenesulfonyl)uracil.

23. The 5-fluorouracil derivative according to claim 11 wherein R$_2$ is β-naphthyl and the compound is 5-fluoro-1-(naphthalene-β-sulfonyl)uracil.

24. The 5-fluorouracil derivative according to claim 11 wherein R$_2$ is p-bromophenyl and the compound is 1-(p-bromobenzenesulfonyl)-5-fluorouracil.

25. The 5-fluorouracil derivative according to claim 11 wherein R$_2$ is 2-thiofuryl and the compound is 5-fluoro-1-(2-thiophenesulfonyl)uracil.

26. The 5-fluorouracil derivative according to claim 11 wherein R$_2$ is 8-quinolyl and the compound is 5-fluoro-1-(8-quinolinesulfonyl)uracil.

27. The 5-fluorouracil derivative according to claim 11 wherein R$_2$ is camphoryl and the compound is 1-(d-camphorsulfonyl)-5-fluorouracil.

* * * * *